(12) United States Patent
Hyun et al.

(10) Patent No.: US 8,582,839 B2
(45) Date of Patent: Nov. 12, 2013

(54) ULTRASOUND SYSTEM AND METHOD OF FORMING ELASTIC IMAGES CAPABLE OF PREVENTING DISTORTION

(75) Inventors: Dong Gyu Hyun, Seoul (KR); Mok Kun Jeong, Seoul (KR)

(73) Assignee: Samsung Medison Co., Ltd., Hongchun-gun (KR)

( * ) Notice: Subject to any disclaimer, the term of this patent is extended or adjusted under 35 U.S.C. 154(b) by 1360 days.

(21) Appl. No.: 12/053,046

(22) Filed: Mar. 21, 2008

(65) Prior Publication Data

US 2008/0232660 A1 Sep. 25, 2008

(30) Foreign Application Priority Data

Mar. 23, 2007 (KR) .................. 10-2007-0028671

(51) Int. Cl.
*G06T 7/20* (2006.01)
*G06T 7/00* (2006.01)

(52) U.S. Cl.
CPC .................................... *G06T 7/0089* (2013.01)
USPC ......................................... 382/128; 382/256

(58) Field of Classification Search
USPC ......................................................... 382/128
See application file for complete search history.

(56) References Cited

U.S. PATENT DOCUMENTS

| | | | |
|---|---|---|---|
| 6,508,768 B1 | 1/2003 | Hall et al. | |
| 6,558,324 B1 * | 5/2003 | Von Behren et al. | ......... 600/440 |
| 6,913,574 B2 | 7/2005 | Jeong et al. | |
| 7,628,754 B2 | 12/2009 | Matsumura et al. | |
| 2002/0178833 A1 | 12/2002 | Chen et al. | |
| 2005/0267368 A1 | 12/2005 | Boctor et al. | |
| 2005/0283076 A1 | 12/2005 | Hangiandreou et al. | |
| 2006/0173320 A1 | 8/2006 | Radulescu | |
| 2007/0016036 A1 | 1/2007 | Nishiura | |
| 2007/0038101 A1 | 2/2007 | Yoon et al. | |
| 2008/0226032 A1 * | 9/2008 | Li et al. | .................. 378/128 |
| 2008/0269606 A1 | 10/2008 | Matsumura | |
| 2009/0124903 A1 | 5/2009 | Osaka | |

FOREIGN PATENT DOCUMENTS

| | | |
|---|---|---|
| EP | 1 900 328 A1 | 3/2008 |
| JP | 2004-261198 | 9/2004 |
| JP | 2005-270341 | 10/2005 |
| JP | 2006-325686 | 12/2006 |
| JP | 2008-508056 | 3/2008 |

(Continued)

OTHER PUBLICATIONS

A. Pesavento, et al., Real time strain imaging and in-vivo applications in prostate cancer, 2001 IEEE Ultrasonics Symposium , Atlanta Ga, Oct. 7-10, 2100, New York Ny, : IEEE, US, vol. 2, Oct. 7, 2001, pp. 1647-1652, XP010584829.

(Continued)

*Primary Examiner* — Robert Kim
*Assistant Examiner* — Eliza Osenbaugh-Stewart
(74) *Attorney, Agent, or Firm* — Oblon, Spivak, McClelland, Maier & Neustadt, L.L.P.

(57) ABSTRACT

The present invention is directed to an ultrasound system and a method of forming an elastic image, which are capable of preventing the distortion of the elastic image. The persistence of the previous frame and the present frame is performed after moving the boundary pixels set up in the previous interest frame to the boundary pixels in the present interest frame. This is so that the distortion of the elastic image may be reduced and the signal to noise ratio may be increased.

7 Claims, 8 Drawing Sheets

(56) References Cited

FOREIGN PATENT DOCUMENTS

| | | |
|---|---|---|
| KR | 10-0483631 | 4/2005 |
| KR | 10-0686288 | 2/2007 |
| WO | WO 2005/120358 A1 | 12/2005 |
| WO | WO 2006/026008 A2 | 3/2006 |
| WO | WO 2006/054635 A1 | 5/2006 |

OTHER PUBLICATIONS

Japanese Office Action issued Mar. 19, 2013, in Japan Patent Application No. 2008-076285.

* cited by examiner

ULTRASOUND SYSTEM AND METHOD OF FORMING ELASTIC IMAGES CAPABLE OF PREVENTING DISTORTION

The present application claims priority from Korean Patent Application No. 10-2007-0028671 filed on Mar. 23, 2007, the entire subject matter of which is incorporated herein by reference.

BACKGROUND OF THE INVENTION

1. Technical Field

The present invention generally relates to ultrasound systems, and more particularly to an ultrasound system and a method of forming elastic images capable of preventing distortion.

2. Background Art

An ultrasound system, which has been widely used in the field of medical diagnosis, transmits ultrasound signals to a target and receives echo signals reflected from the target to form an ultrasound image. A brightness-mode (B-mode) is a representative ultrasound image display mode, which is expressed with reflection coefficients of tissues depending on acoustic impedance differences between the tissues. However, it is difficult to observe a tissue having the reflection coefficient not lager than those of neighboring tissues such as a tumor.

Tissues such as tumor or cancer can be found with the elastography showing the mechanical characteristics of the tissues (i.e., elastography images of tissues), which cannot be diagnosed with the B-mode ultrasound image. Thus, the elastography is very helpful to diagnose resins.

In order to form an elastic image, reference signals are formed with reflective signals from the target prior to applying pressure to the target and receive signals are formed with other reflective signals from the target to which the pressure is applied. The displacement of the target due to the pressure is obtained with the difference between the reference signals and the receive signals, i.e., the delay time between the reference signals and the receive signals.

While forming the ultrasound image by applying the pressure to the target through a probe, the target moves in upward, downward, left or right directions due to the pressure, density distribution of a medium or density of the tissues around the target. Thus, the target is not located on a fixed position in the image frames. That is, in such a case of forming image frames $F_1$, $F_2$ and $F_3$ with applying pressure to target T (shown in FIG. 1), the position of target T is not fixed on one fixed position even though the density of a medium M is uniform. If the variation of the target's position is ignored in forming the elastic image of the target, then distortion is generated.

In order to prevent the generation of distortion, various methods such as an optical flow, a 2-dimensional correlation and a block matching have been adopted to correct the positions of the target in image frames. However, such conventional methods require a significant amount of calculation and take a long process time. Thus, the capability of a processor should be guaranteed above a certain level.

BRIEF DESCRIPTION OF THE DRAWINGS

Arrangements and embodiments may be described in detail with reference to the following drawings in which like reference numerals refer to like elements and wherein.

DETAILED DESCRIPTION OF THE INVENTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

Figure 1:
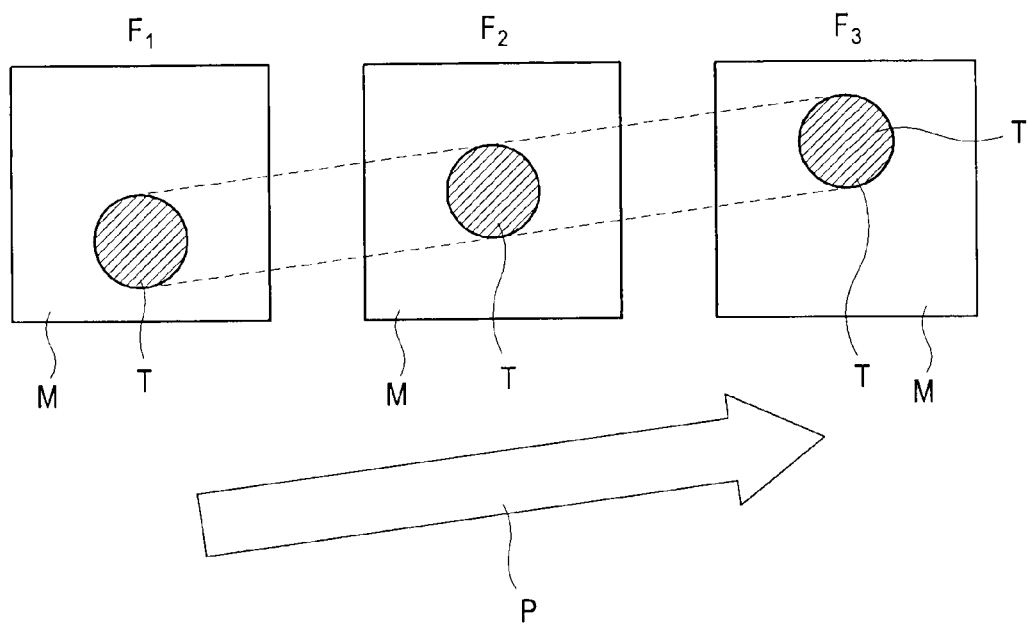
FIG. 1 is a schematic diagram showing a variation of target's positions in a plurality of ultrasound images with pressure applied to the target.
Figure 2:
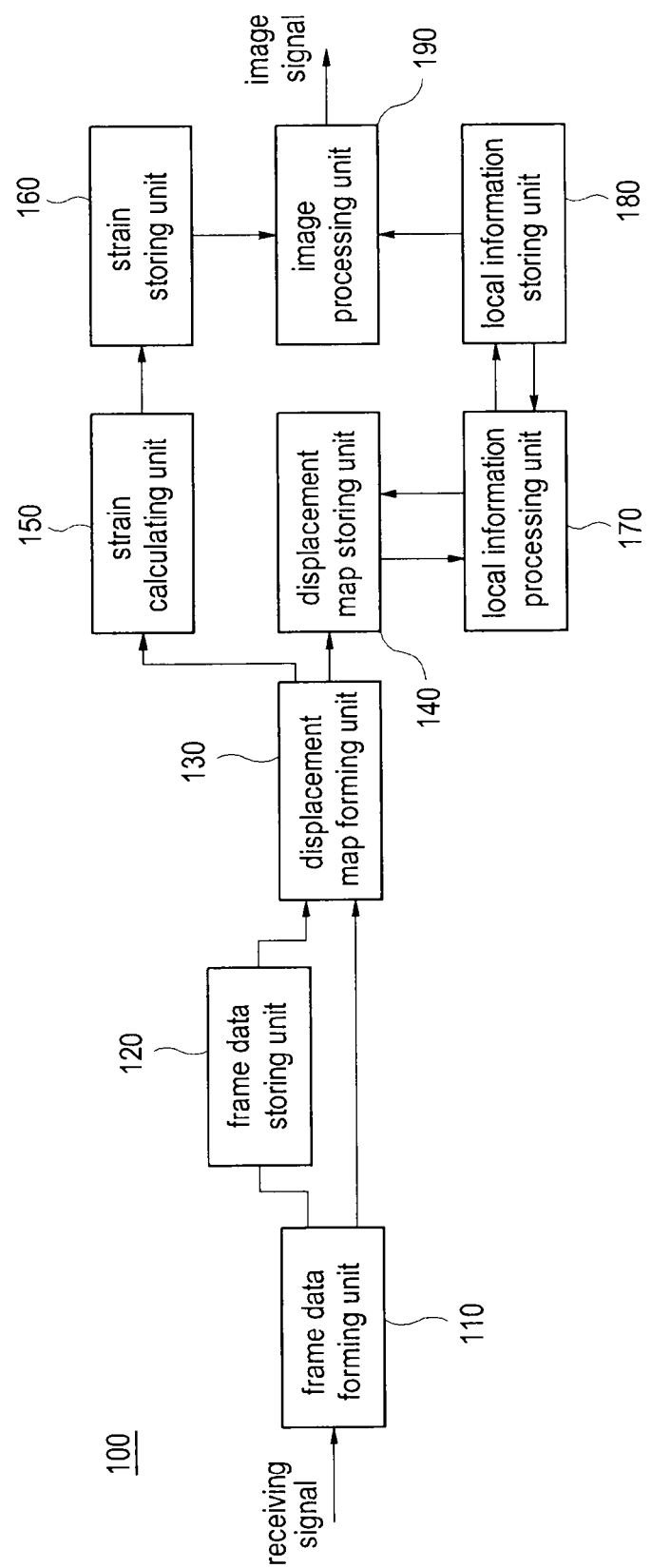
FIG. 2 is a schematic diagram showing an example of an ultrasound imaging system in accordance with the present invention.

Referring to FIG. 2, the ultrasound system 100 includes a frame data forming unit 110, a frame data storing unit 120, a displacement map forming unit 130, a displacement map storing unit 140, a strain calculating unit 150, a strain storing unit 160, a local information processing unit 170, a local information storing unit 180 and an image processing unit 190.

The frame data forming unit 110 is configured to form frame data with receive signals provided from an ultrasound diagnosis unit (not shown). The receive signals may be RF signals or IQ signals. The frame data include reference frame data formed with reflective signals from the target without applying pressure and interest frame data formed with other reflective signals from the target undergoing the pressure. A plurality of the interest frames may be formed periodically one after another by applying the pressure to the target. The reference frame data and the interest frame data may be stored in the frame data storing unit 120 and may be inputted to the displacement map forming unit 130.

The displacement map forming unit 130 forms a displacement map of the interest frame by comparing the interest frames with the reference frame. The displacement map may be formed with the conventional methods, i.e., phase differences between the reference frame and the interest frames are calculated with the conventional methods such as the cross correlation or the autocorrelation of complex baseband signals to form the displacement. The displacement map may be formed by comparing all or some pixels of the reference frame and the interest frames. In addition, the displacement map forming unit 130 applies a space filter to the displacement maps of the interest frames for reducing noise. A median filter or an average filter may be utilized as the space filter. The filtered displacement maps of the interest frames are stored in the displacement map storing unit 140.

The strain calculating unit 150 calculates strains of the interest frames with the use of the displacement maps. The strains may be calculated with the gradient method of obtaining the displacement per unit length. In such a case of forming the displacement maps by comparing all of the pixels in the reference frames and the interest frame, the strains of all the pixels in the interest frame may be calculated. In such a case of comparing some pixels of the reference frame and the interest frame to form the displacement map, the strains of some pixels may be calculated. The strains of the respective interest frame may be stored in the strain storing unit 160.

Figure 3:
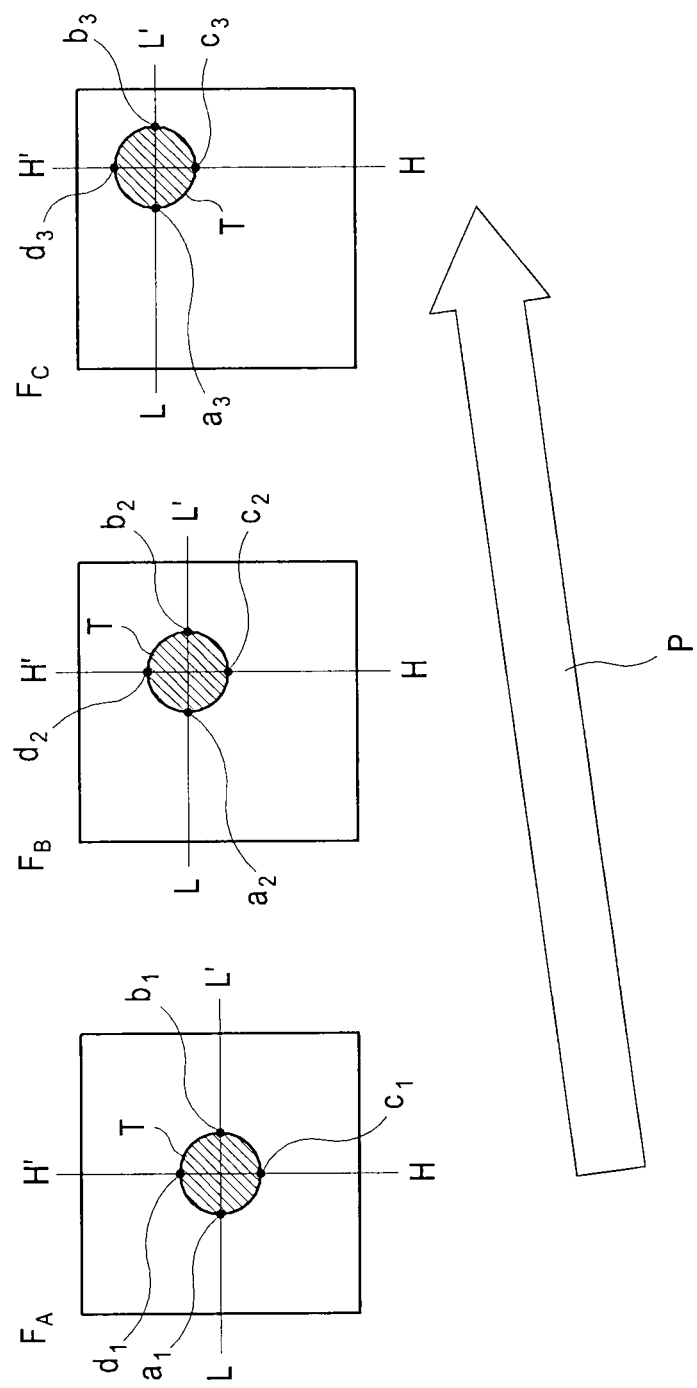
FIG. 3 is a schematic diagram showing a variation of target's position and boundary pixels in a plurality of ultrasound images.
Figure 4:
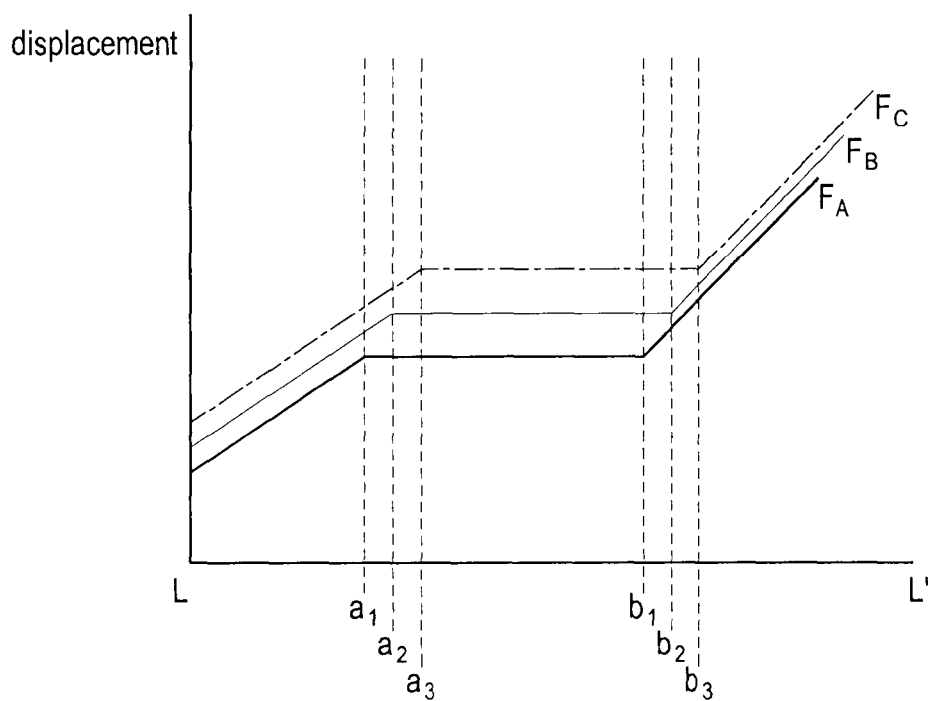
FIG. 4 is a graph showing a variation of displacement in a horizontal direction in the ultrasound images.
Figure 5:
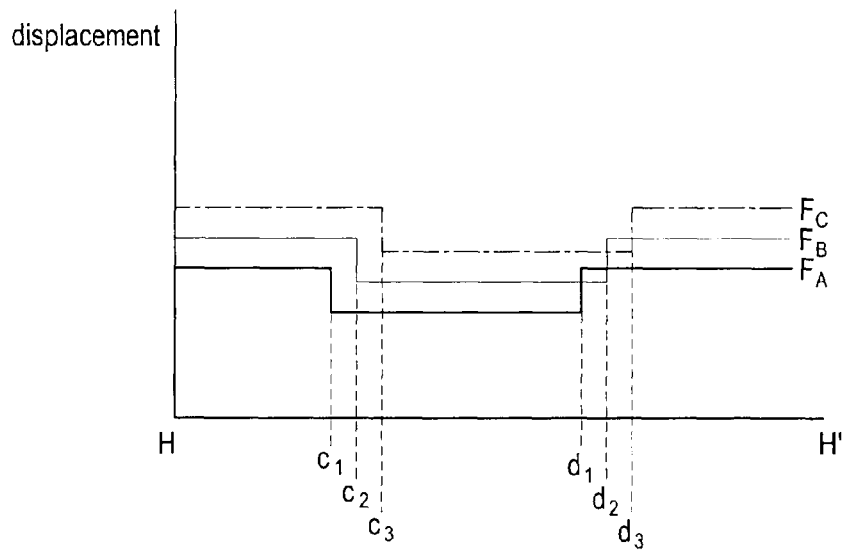
FIG. 5 is a graph showing a variation of displacement in a vertical direction in the ultrasound images.

The local information processing unit 170 receives the displacement map and the strains of the interest frames $F_A$, $F_B$ and $F_C$, which are obtained periodically, one after another when the intensity of the pressure P increases in one direction (shown in FIGS. 3 to 5). The local information processing unit 170 analyzes the strain at each pixel and determines boundary pixels with the pixels where the strain varies, i.e., the boundary pixels are on the boundary of the target T, the strain of which is different from those of the neighboring media. For example, boundary pixels $a_1$ to $a_3$ and $b_1$ to $b_3$ may be determined on horizontal line L-L', as shown in FIGS. 3 and 4, while boundary pixels $c_1$ to $c_3$ and $d_1$ to $d_3$ may be determined on vertical line H-H', as shown in FIGS. 3 and 5. Referring to FIGS. 4 and 5, the variation amount of the displacement according to the position change of the pixels may be the strain. FIGS. 3 to 5 show only some boundary pixels found on the two lines L-L' and H-H'. However, those boundary pixels are only examples, i.e., the local information processing unit 170 may set up the boundary pixels in all the regions in which the displacement or the strain is formed.

Once first boundary pixels are set up in the $n^{th}$ interest frame, the local information processing unit 170 may move the first boundary pixels of the $n-1^{th}$, interest frame to positions corresponding to the first boundary pixels of $n^{th}$ interest frame to set up second boundary pixels in the $n-1^{th}$ interest frame. Hereinafter, the second boundary pixel in the respective interest frame is also referred to as the moved pixel.

Figure 6:
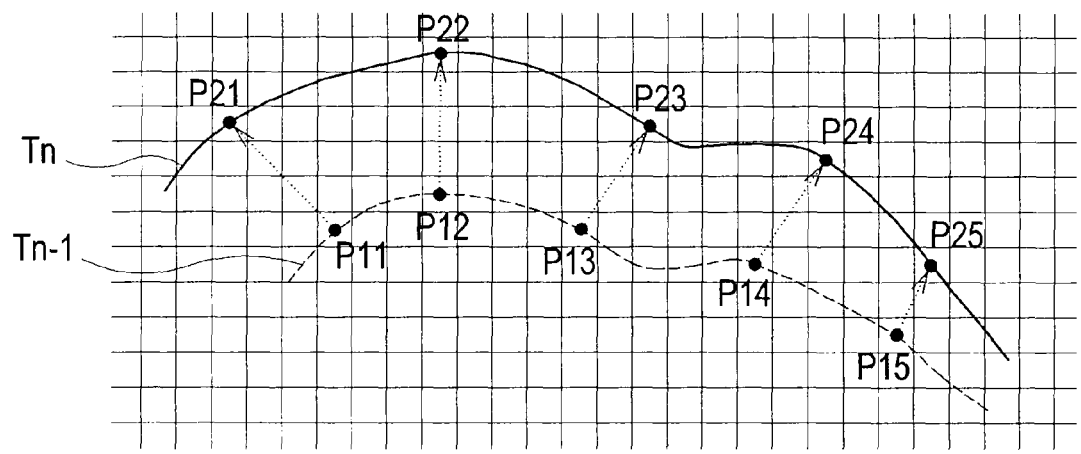
FIGS. 6 and 7 are schematic diagrams illustrating the addition or deduction of pixels between moved boundary pixels.

Since the moved pixels are obtained by changing the position of the first boundary pixels, it is assumed that the pixels may be increased or decreased between the moved pixels. Referring to FIG. 6, if first boundary pixels P11, P12, P13, P14 and P15 on a target boundary Tn−1 in the $n-1^{th}$ interest frame are moved to positions of the first boundary pixels on a target boundary Tn in the $n^{th}$, interest frame to obtain the second boundary pixels P21, P22, P23, P24 and P25, then the numbers of pixels between two first boundary pixels are changed. For instance, the pixel number between the two pixels P11 and P12 is different from the pixel number between the two pixels P21 and P22.

Figure 7:
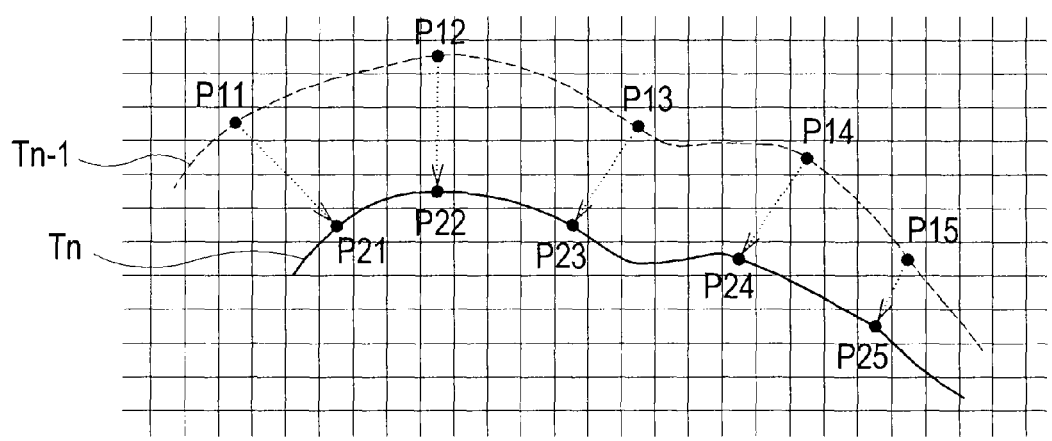

As shown in FIG. 6, when the number of pixels between the second boundary pixels P21 and P23 is larger than that between the first boundary pixels P11 and P13 on the same row, it is assumed that pixels are added between the two second boundary pixels, i.e., between the two moved pixels. The moved pixels may have the original strain. However, the strain of the added pixels is zero. Referring to FIG. 7, when the number of the pixels between the two moved pixels P21 and P23 is smaller than that between the first boundary pixels P11 and P13, it is assumed that image pixels are omitted between the two moved image pixels. The local information storing unit 180 stores the positions and strains of the first and second boundary pixels.

The image processing unit 190 reconstructs the $n-1^{th}$ interest frame with the second boundary pixels. For instance, the image processing unit 190 searches the pixels having a zero strain (i.e., the added pixels) and forms inferred strains of the added pixels in consideration of the strains of moved pixels adjacent to the added pixels in the same row or column. The inferred strain of the added pixel may be identical to that of the most adjacent moved pixel. Also, the inferred strain of the added pixel may be obtained by applying weight values to the strains of two adjacent pixels in consideration of the distances between the added pixel and the two adjacent pixels. Further, the image processing unit 190 forms an elastic image by performing persistence with the reconstructed $n-1^{th}$ interest frame and the $n^{th}$ interest frame. The persistence may be performed in accordance with the following Equation 1.

$$S_k(i,j)=P \times S_{k-1}(i,j)+(1-P) \times X_k(i,j) \qquad \text{Eq. (1)}$$

Equation 1 denotes that pixel value $S_k(i, j)$ of a pixel located at $(i, j)$ in the $n^{th}$ interest frame is obtained with strain $X_k$ of the pixel and the pixel value $S_{k-1}$ of the other pixel located at $(i, j)$ in the $n-1^{th}$ interest frame. In Equation 1, P denotes a persistence ratio.

The frame data forming unit 110, the displacement map forming unit 130, the strain calculating unit 150, the local information processing unit 170 and the image processing unit 190 may be configured with one processor or respective processors. The frame data storing unit 120, the displacement map storing unit 140, the displacement strain storing unit 160 and the local information storing unit may be configured with one memory or respective memories.

Figure 8:
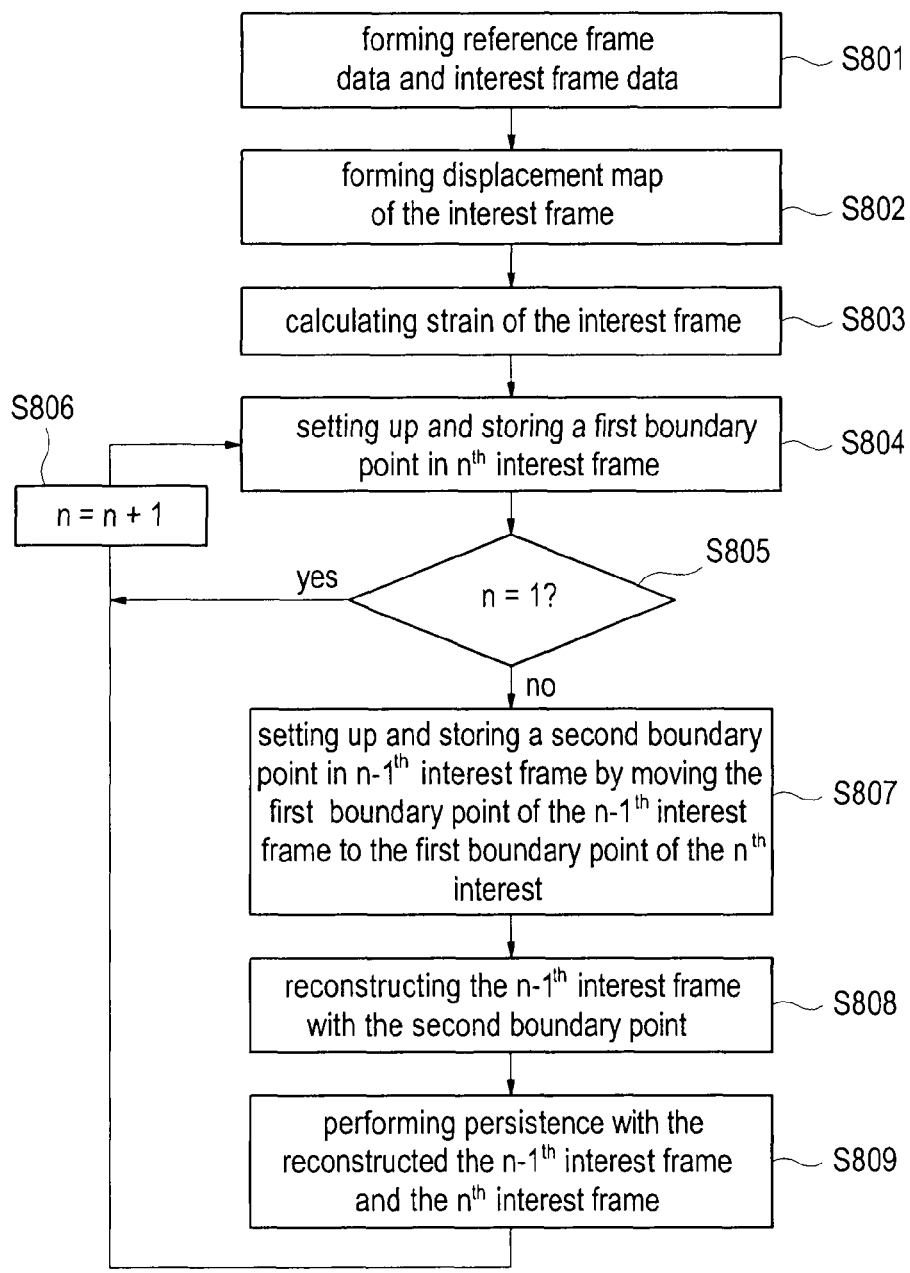
FIG. 8 is a flow chart showing a procedure of forming an elastic image in accordance with the present invention.
Figure 9:
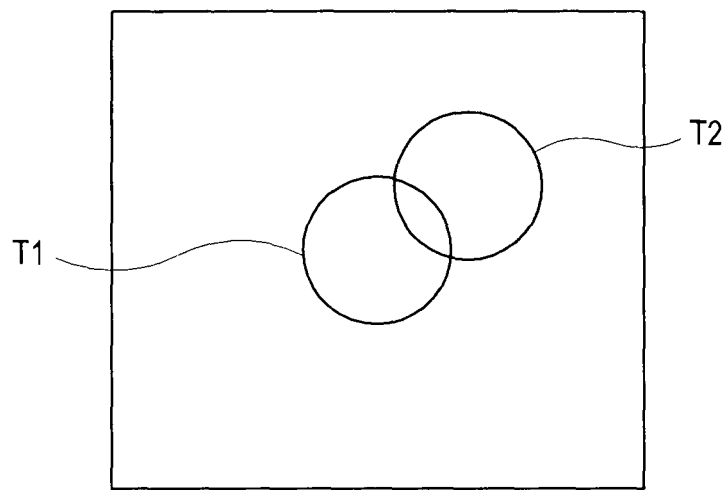
FIGS. 9 and 10 are diagrams illustrating a persistence result of the present invention in comparison with the conventional method.
Figure 10:
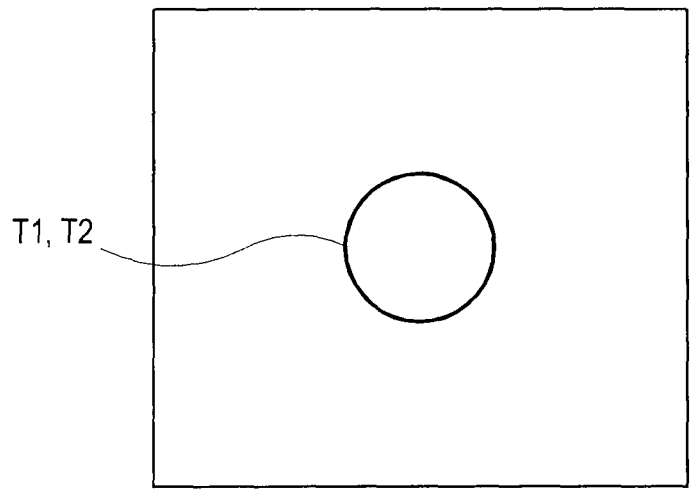

FIG. 8 shows the method of forming elastic images in accordance with another embodiment of the present invention.

A reference frame data is formed with reflective signals from a target prior to applying pressure to the target. Further, an interest frame data is formed with other reflective signals from the target, which is undergoing the pressure (step S801).

Displacement maps of the interest frames are formed by comparing the interest frames with the reference frame (S802). The displacement map may be formed by comparing all or some pixels of the reference frame and the interest frame. The strains of the interest frames are calculated by using the displacement maps (S803).

The strain of each pixel is analyzed. First boundary pixels are set up with the pixels where the strains vary, in the $n^{th}$ interest frame, and the position of the first boundary pixels of the $n^{th}$ interest frame are stored (S804). Herein, "n" is a natural number denoting the order of the interest frame and the initial value of the "n" is one.

It is determined whether the $n^{th}$ interest frame is the first interest frame or not (S805). In such a case of the first interest frame, the number "n" is increased by one and processes mentioned above are preformed again (S806). In such a case where the $n^{th}$ interest frame is not the first interest frame, the first boundary pixels of the $n-1^{th}$ interest frame interest are moved to the positions corresponding to the first boundary pixels of $n^{th}$ interest frame to set up second boundary pixels in the $n-1^{th}$ interest frame and the second boundary pixels are stored (S807).

The $n-1^{th}$ interest frame is reconstructed with the use of the second boundary pixels (S808). In reconstructing the $n-1^{th}$ interest frame, the inferred strains of added pixels between the second boundary pixels may be calculated in accordance with the foregoing embodiment.

An elastic image is formed by performing persistence with the reconstructed n−1 th interest frame and the n th interest frame (S809). The process is then iteratively performed for each of a plurality of $n^{th}$ interest frames and $n-1^{th}$ interest frames by increasing the number "n" by one and performing the processes mentioned above again (S806). The persistence may be performed in accordance with the foregoing embodiment.

Further, in accordance with another embodiment of the present invention, a computer readable medium may store a program for performing the method mentioned above.

In the present invention, the persistence of the previous frame and the present frame is performed after moving the boundary pixels set up in the previous interest frame to the boundary pixels in the present interest frame. This is so that the distortion of the elastic image may be reduced and the signal to noise ratio (SNR) may be increased. In other words, in case of performing the persistence with the boundary pixels of the two frames without meeting the positions of the boundary pixels as the conventional method, the targets T1 and T2 in each interest frame do not meet and the distortion is generated and a distorted elastic image is obtained. However, in the present invention, the boundary pixels of the n−1$^{th}$ and the n$^{th}$ interest frames are met with each other prior to performing the persistence. Thus, the positions of the targets T1 and T2 in each interest frame are identical and more apparent elastic image may be obtained. Accordingly, the present invention is capable of preventing the distortion due to the pressure applied to the target in the process of forming the elastic image.

Any reference in this specification to "one embodiment," "an embodiment," "example embodiment," etc. means that a particular feature, structure or characteristic described in connection with the embodiment is included in at least one embodiment of the present invention. The appearances of such phrases in various places in the specification are not necessarily all referring to the same embodiment. Further, when a particular feature, structure or characteristic is described in connection with any embodiment, it is submitted that it is within the purview of one skilled in the art to effect such feature, structure or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound system, comprising:
   a frame data forming unit configured to form reference frame data with reflective signals from a target prior to applying pressure to the target and interest frame data of a plurality of interest frames with other reflective signals from the target undergoing the pressure;
   a displacement map forming unit configured to form displacement maps of the interest frames by comparing the interest frames with the reference frame;
   a strain calculating unit configured to calculate the strains of interest frames with the use of the displacement maps;
   a local information processing unit configured to analyze the strain at each pixel to determine pixels where the strain varies as first boundary pixels on each interest frame, wherein the local information processing unit is configured to analyze the strains of a n$^{th}$ interest frame and set up first boundary pixels in the n$^{th}$ interest frame, and to move first boundary pixels set up in a n−1$^{th}$ interest frame to corresponding positions of the first boundary pixels of the n$^{th}$ interest frame to obtain second boundary pixels; and
   an image processing unit configured to reconstruct the n−1$^{th}$ interest frame with the second boundary pixels and to perform persistence with the reconstructed n−1$^{th}$ interest frame and the n$^{th}$ interest frame, wherein the processes performed by the local information processing unit and the image processing unit are iteratively performed for each of a plurality of n$^{th}$ interest frames and n−1$^{th}$ interest frames.

2. The ultrasound system of claim 1, wherein the image processing unit is configured to search additional pixels having a zero strain between the second boundary pixels in the n−1$^{th}$ interest frame and form inferred strain of the additional pixels from the strains of the second boundary pixels adjacent thereto in the same row or column, the image processing unit being further configured to set up the inferred strain as the strain of the additional pixel.

3. The ultrasound system of claim 1, further comprising:
   a storing unit configured to store the displacement maps, the strains, the positions and the strains of the first and second boundary pixels.

4. A method of forming an elastic image, comprising:
   forming a reference frame data with reflective signals from a target prior to applying pressure to the target;
   forming interest frame data of a plurality of interest frames with other reflective signals from the target undergoing the pressure;
   forming displacement maps of the interest frames by comparing the interest frames with the reference frame;
   calculating strains of the interest frames by using the displacement maps;
   analyzing the strains of the interest frames to determine pixels where the strain varies as first boundary pixels in the interest frames, wherein the strains of a n$^{th}$ interest frame are analyzed to set up first boundary pixels in the n$^{th}$ interest frame;
   moving first boundary pixels set up in a n−1$^{th}$ interest frame to corresponding positions of the first boundary pixels of the n$^{th}$ interest frame to obtain second boundary pixels;
   reconstructing the n−1$^{th}$ interest frame with second boundary pixels; and
   forming an elastic image by performing persistence with the reconstructed n−1$^{th}$ interest frame and the n$^{th}$ interest frame, wherein
   the analyzing, the moving, the reconstructing and the forming are iteratively performed for each of a plurality of n$^{th}$ interest frames and n−1$^{th}$ interest frames.

5. The method of claim 4, wherein the step of reconstructing the n−1$^{th}$ interest frame includes:
   searching additional pixels having a zero strain between the second boundary pixels in the n−1$^{th}$ interest frame;
   forming inferred strains of the additional pixels from the strains of the second boundary pixels adjacent thereto in the same row or column; and
   setting up the inferred strain as the strain of the additional pixel.

6. A computer readable medium storing a program for performing a method of forming an elastic image, the method comprising:
   forming a reference frame data with reflective signals from a target prior to applying pressure to the target;
   forming interest frame data of a plurality of interest frames with other reflective signals from the target undergoing the pressure;
   forming displacement maps of the interest frames by comparing the interest frames with the reference frame;
   calculating strains of the interest frames by using the displacement maps;
   analyzing the strains of the interest frames to determine pixels where the strain varies as first boundary pixels in the interest frames, wherein the strains of a $n^{th}$ interest frame are analyzed to set up first boundary pixels in the $n^{th}$ interest frame;

moving first boundary pixels set up in a $n-1^{th}$ interest frame to corresponding positions of the first boundary pixels of the $n^{th}$ interest frame to obtain second boundary pixels;

reconstructing the $n-1^{th}$ interest frame with second boundary pixels; and forming an elastic image by performing persistence with the reconstructed $n-1^{th}$ interest frame and the $n^{th}$ interest frame, wherein the analyzing, the moving, the reconstructing and the forming are iteratively performed for each of a plurality of $n^{th}$ interest frames and $n-1^{th}$ interest frames.

7. The computer readable medium of claim 6, wherein the step of reconstructing the $n-1^{th}$ interest frame includes:

searching additional pixels having zero strain between the second boundary pixels in the $n-1^{th}$ interest frame;

forming inferred strains of the additional pixels from the strains of the second boundary pixels adjacent thereto in the same row or column; and setting up the inferred strain as the strain of the additional pixel.

\* \* \* \* \*